(12) United States Patent
Brückl et al.

(10) Patent No.: US 9,068,978 B2
(45) Date of Patent: Jun. 30, 2015

(54) OPTICAL MEASUREMENT METHOD FOR MOLECULAR DETECTION USING RELAXATION MEASUREMENT IN OPTICALLY ANISOTROPIC NANOPARTICLES AND DEVICE FOR PERFORMING THE METHOD

(75) Inventors: Hubert Brückl, Wiener Neudorf (AT); Jörg Schotter, Vienna (AT); Ole Bethge, Vienna (AT)

(73) Assignees: Tecnet Equity NOE Technologiebeteiligungs-Invest GmbH, St. Poelton (AT); AIT Austrian Institute of Technology GmbH, Vienna (AT)

( * ) Notice: Subject to any disclaimer, the term of this patent is extended or adjusted under 35 U.S.C. 154(b) by 1338 days.

(21) Appl. No.: 12/578,484

(22) Filed: Oct. 13, 2009

(65) Prior Publication Data

US 2010/0105026 A1   Apr. 29, 2010

Related U.S. Application Data

(63) Continuation of application No. PCT/AT2008/000110, filed on Mar. 27, 2008.

(30) Foreign Application Priority Data

Apr. 11, 2007   (AT) .................................. A 560/2007

(51) Int. Cl.
*G01N 33/553* (2006.01)
*G01N 33/543* (2006.01)
(Continued)

(52) U.S. Cl.
CPC .......... *G01N 33/54346* (2013.01); *B82Y 15/00* (2013.01); *B82Y 30/00* (2013.01); *G01N 21/1717* (2013.01); *G01N 2021/258* (2013.01)

(58) Field of Classification Search
CPC .... B82Y 15/00; B82Y 30/00; G01N 21/1717; G01N 33/54346; G01N 2021/258
USPC .................................................. 436/518, 526
See application file for complete search history.

(56) References Cited

U.S. PATENT DOCUMENTS 4,884,886 A * 12/1989 Salzman et al. ............... 356/367
6,027,946 A   2/2000 Weitschies et al.
(Continued)

FOREIGN PATENT DOCUMENTS

| WO | 9623227 A1 | 8/1996 |
|---|---|---|
| WO | 0111360 A2 | 2/2001 |
| WO | 03019188 A1 | 3/2003 |

OTHER PUBLICATIONS

Crespo et al. "Permanent magnetism, magnetic anisotropy, and Hysteresis of Thiol-capped gold nanoparticles". Phys. Rev. Lett. vol. 93, No. 8, 2004, 087204-1-4.*

(Continued)

*Primary Examiner* — Bao Thuy L Nguyen
*Assistant Examiner* — Pensee Do
(74) *Attorney, Agent, or Firm* — Laurence A. Greenberg; Werner H. Stemer; Ralph E. Locher

(57) ABSTRACT

Optical measurement methods are described that are suitable for determining the relaxation behavior of nanoparticles dispersed in a solution. The particles have optically anisotropic properties and are alignable by an external stimulus, for example, an electric or magnetic field. In this manner the optical detection of certain molecules that can bind specifically to the surface of the nanoparticles and thus change the relaxation behavior of the nanoparticles as well as to provide devices for carrying out the methods is possible.

16 Claims, 2 Drawing Sheets

(51) Int. Cl.
  *B82Y 15/00* (2011.01)
  *B82Y 30/00* (2011.01)
  *G01N 21/17* (2006.01)
  *G01N 21/25* (2006.01)

(56) References Cited

U.S. PATENT DOCUMENTS

| | | |
|---|---|---|
| 6,485,985 B1 | 11/2002 | Weitschies et al. |
| 6,825,655 B2 | 11/2004 | Minchole et al. |
| 6,979,574 B1 | 12/2005 | Kötitz et al. |
| 2006/0008924 A1 | 1/2006 | Anker et al. |
| 2006/0068203 A1* | 3/2006 | Ying et al. .................... 428/403 |
| 2006/0233712 A1* | 10/2006 | Penades et al. .............. 424/9.34 |
| 2009/0033935 A1* | 2/2009 | Chung et al. .................. 356/338 |

OTHER PUBLICATIONS

Hao et al. "Synthesis and Optical properties of Anisotropic metal nanoparticles" Journal of Fluorescence, vol. 14, No. 4, Jul. 2004.*
International Search Report dated Jun. 27, 2008.
Glöckl, et al: "Development of a Liquid Phase Immunoassay by Time-Dependent Measurements of the Transient Magneto-Optical Birefringence Using Functionalized Magnetic Nanoparticle", Journal of Magnetism and Magnetic Materials 289, (2005), Nov. 30, 2004, pp. 480-483, Germany.

* cited by examiner

OPTICAL MEASUREMENT METHOD FOR MOLECULAR DETECTION USING RELAXATION MEASUREMENT IN OPTICALLY ANISOTROPIC NANOPARTICLES AND DEVICE FOR PERFORMING THE METHOD

CROSS-REFERENCE TO RELATED APPLICATION

This application is a continuation, under 35 U.S.C. §120, of copending international application No. PCT/AT2008/000110, filed Mar. 27, 2008, which designated the United States; this application also claims the priority, under 35 U.S.C. §119, of Austrian patent application No. A 560/2007, filed Apr. 11, 2007; the prior applications are herewith incorporated by reference in their entirety.

BACKGROUND OF THE INVENTION

Field of the Invention

The invention relates to a novel detection method for a molecular detection procedure, in which the target molecules to be detected bind specifically to the surface of nanoparticles that are suspended in an appropriate solution and functionalized appropriately. As a result of the binding, the hydrodynamic diameters of the particles increase. If the alignment of the particles is now changed by an external stimulus, then the increase in the hydrodynamic diameters leads to a change in the Brownian relaxation behavior of the nanoparticles. The measurement of the relaxation behavior then allows the quantification of the concentration of the target molecules in the solution.

The measurement of the relaxation behavior for determining the occupation of nanoparticles by molecules was published for the first time by Weitschies et al. in international patent publication WO 96/23227 A1 (corresponding to U.S. Pat. Nos. 6,027,946 and 6,485,985), where ferromagnetic or ferrimagnetic nanoparticles are described, whose magnetic moments are aligned in an external magnetic field. The particles here have constitutions such that the Néel relaxation time of the particle magnetization is greater than the Brownian relaxation time, where the latter is a function of the hydrodynamic diameter of the particle, which increases in the case of addition of molecules. For example, after a magnetic field that aligns the particles has been switched off, the temporal course of the relaxation of the magnetic moment of the particle set is recorded by use of an appropriate sensor, which makes it possible to derive the earlier average occupation by molecules of the particle set. As sensors, one can use SQUIDs, induction coils, flux gates or magneto-resistive elements for this purpose. The particles are either free in solution or bound specifically by or via capturing ring molecules (h) to surfaces.

Minchole et al. describe a similar method in international patent disclosure WO 03/019188 A1 (corresponding to U.S. Pat. No. 6,825,655), which relates to the same process principle, although it presents an alternative measurement method that is based on the recording of a magnetic AC susceptibility spectrum of the particle set, from which one can also determine the average relaxation time of the magnetic particles.

However, all the patent applications and patents as well as the publications concerning the molecular detection by relaxation measurements with nanoparticles that have been published to date share the feature that until now purely magnetic particles as well as methods based on magnetism were used exclusively. However, particularly in reference to the measurement of relaxation, "magnetic" measurement methods have the disadvantage that the magnetic moment of the particle set used is very small, and the magnetic scattered fields weaken very rapidly with removal from the particle, which results in the need for either highly sensitive, but expensive, sensors, such as SQUIDs, or, on the other hand, the sensors have to be placed in very close spatial proximity to the particles, which considerably limits the practical usability of the overall system as well as the reproducibility of the measurement results.

Optical measurement methods, on the other hand—as was found—present the advantage of excellent sensitivity and simultaneously high equipment tolerance. In particular, the parameter value of extinction is largely independent of separation and thus allows the construction of a flexible device with high sample throughput and good reproducibility and sensitivity of the measurement results. No study has been published to date on optical measurement methods for the relaxation of nanoparticles.

In conventional biotechnology, numerous optically active elements are used. The palette ranges from organic fluorescent dyes to semiconducting nanocrystals, also called quantum dots, for example, CdSe or ZnS nanoparticles, to nanoparticles made of noble metals, such as, Au or Ag, in which plasmon resonances can be excited by incident light, which results in a very characteristic scattering and extinction spectrum. In most applications, these optical elements are used exclusively as a label, to demonstrate the presence of certain specific marked molecules. In these applications, the molecule-label complexes must be bound, usually specifically, to surfaces, allowing the removal of unbound label in subsequent washing steps, which prevents unbound labels from biasing the analysis results.

However, the binding effectiveness of molecules to surfaces is lower in comparison with processes in the free solution, and the analysis time is increased considerably compared to volumetric reactions, because of the required diffusion of the molecules to be detected toward the functionalized surface. In addition, the surface functionalizations are too expensive for numerous applications intended only for the rapid determination of the concentration of a few target molecule species in a certain volume of solution.

However, to distinguish between bound and unbound labels in volumetric methods, procedures are required in which the labels themselves change at least one measurable property, when target molecules are bound specifically to them.

In the field of optical DNA detection, it is possible, for example, to use so-called molecular beacons, in which the fluorescent resonant energy transfer (FRET) effect in the unbound state of the label suppresses fluorescence emission. It is only at the time when the target sequence docks to the label that the molecular beacon opens, and donor and acceptor are separated spatially from each other allowing fluorescence emission of the label occurs. However, the use of the molecular beacons is limited to the detection of relatively short DNA and RNA strands, i.e., for example, proteins cannot be detected in this way.

Au or Ag nanoparticles are an additional example of active labels in biotechnology in which, due to a change in the plasmon resonance condition, the absorption and emission spectra are shifted when molecules dock to the particle surface. However, this shift is quite small, and consequently the detection limit for proteins with this system is restricted typically to the lower μM range.

An additional variant of active labels is described in U.S. patent publication No. 2006/0008924 A1 (Anker et al.). Here, magnetic nanoparticles that have been passivated on one side are presented, in which the fluorescence-labeled target molecules are capable of binding specifically to only one of the two semispherical surfaces of the label. If the labels are then shifted in rotation by an alternating magnetic field, and fluorescence is observed in only a limited spatial angle, then the fluorescence-labeled target molecules that are bound to the labels blink in the rotation frequency, and can thus be distinguished from unbound fluorescent dyes and other background signals. However, there is no connection between this detection method and the optical relaxation measurements that are the foundation of the present invention.

SUMMARY OF THE INVENTION

It is accordingly an object of the invention to provide an optical measurement method for molecular detection using relaxation measurement in optically anisotropic nanoparticles and device for performing the method, which overcomes the above-mentioned disadvantages of the prior art devices of this general type.

With the foregoing and other objects in view there is provided, in accordance with the invention, a method for molecular detection via determination or measurement of a relaxation behavior of particles being either microparticles or nanoparticles, that are dispersed or suspended in a fluid medium. On a surface of the particles, target molecules, molecule sequences, molecule parts or organisms are bound specifically or nonspecifically. The particles that have been occupied in this way are alignable, at least predominantly, in a spatial direction, in the dispersion or the suspension, as a result of an influence of an external stimulus. For the determination of the relaxation behavior, in the suspension or the dispersion being used the particles have optical anisotropy, besides their geometric positional alignability, where the optical anisotropy of the particles originates from an anisotropic particle excitation in the particles. The particles, in the dispersion or the suspension, are converted either from an at first stochastic, statistically disordered, unaligned state, into a finally at least predominantly uniformly aligned state, or vice versa by irradiating in light with linear light, polarized light or nonpolarized light into the suspension or the dispersion. Behavior or properties of the dispersion or the suspension are determined in each of the two states and/or between the two states resulting in a determined relaxation behavior by subjecting the light to an optometric analysis where the light is: taken up directly from the suspension or the dispersion in an irradiation direction in or by absorption, the light exiting as scattered light at an angle with respect to the irradiation direction, or the light that is emitted by excitation. The optometric analysis is performed immediately, after the light passes through a polarization filter connected after the dispersion or the suspension, and/or only after a forced passage through a polarization filter which is connected after the dispersion or the suspension through which the light passes. From the determined relaxation behavior a concentration, a size and/or a property of one of the target molecules, the molecule sequences, the molecule parts and the organisms bonded to the particles, is determined.

The core of the present invention is thus a new type of detection of particle relaxation by the novel use of anisotropic optical properties of the nanoparticles used. If the spatial alignment of the particle changes, then their optical anisotropy, in an appropriate optical measurement setup, leads to a corresponding optically detectable signal change, which allows the determination of the instantaneous alignment of the particles, where the determination is either absolute or relative to an external stimulus or field. Possible parameter values here are, for example, but not exclusively, the spectrum and/or the polarization of the light that has been scattered, emitted or quenched by the particles.

The core of the present invention is the optical detection of the relaxation of nanoparticles by using optically anisotropic properties of the particles used. Possible parameter values here are, for example, but not exclusively, the spectrum or the polymerization of the light that is scattered, emitted or quenched by the particles. Moreover, the constitution of the particles is such that their spatial alignment in the solution can be changed by an external stimulus, particularly by an external field, such as, for example, by an electric or magnetic field.

The invention thus makes it possible to use optical methods to determine the spatial alignment of the particle relative to the stimulus or field, which allows a measurement of the particle relaxation. If certain target molecules are, in addition, bound specifically to the particle surface, then the measured relaxation behavior allows a quantification of the concentration of the target molecules in the solution. The measurement system used for the novel method thus contains the now described components.

1. An External Stimulus or External Field.

To align the nanoparticles in a defined spatial alignment, an external stimulus must be capable of exerting a moment of force to the particle. This stimulus can be particularly a unidirectional, electric or magnetic, field.

For example, it is known that oblong nanoparticles made of noble metals, such as, Au and Ag, can be aligned directly by the application of electrical fields. However, the required electrical field strengths to achieve a sufficient degree of alignment for practical applications is quite high, see, for example, van der Zande et al., J. Phys. Chem. B 103 (1999) 5754. In addition, by the application of a strong electrical field, the buffer solution as well as the target molecules can also become polarized, which can lead to interfering influences.

Magnetic fields, on the other hand, have the advantage of presenting hardly any interfering effect in biological systems. However, to be able to use magnetic fields for aligning the nanoparticles, they must possess a magnetic moment whose Néel relaxation time is clearly greater than the Brownian relaxation time to be measured. In cases where magnetic particles cannot be used without problem for the optical anisotropy measurements, nonmagnetic nanoparticles that are provided with magnetic components by an appropriate composite structure can be provided, so that such particles which themselves are not magnetic can also be aligned by magnetic fields. Examples of such a composite structure include core-sheath structures or oblong particles with magnetic materials on the poles.

To measure the relaxation behavior of the particles, the amplitude and/or direction of the external stimulus is changed, and the relaxation of the particles toward the equilibrium position resulting from the new stimulus is recorded as a function of time, frequency and/or phase. In the process, individual or periodic changes of the stimulus or field are possible.

An individual measurement can consist, for example, of switching off a previously spatially or temporally constant stimulus, followed then by a new stochastic distribution over time by Brownian relaxation of the anisotropy directions of the nanoparticle set. This is associated with a temporal decrease of the measured optical anisotropy signal of the nanoparticle set, and, from the decay time, it is possible to derive the average occupation of the nanoparticles by target molecules.

An additional possible example for a periodic change of the stimulus is a continuous spatial rotation with constant amplitude. In this case, the measurement signal consists of the phase shift that is recorded at an appropriate rotation frequency, between the direction of the stimulus and the measured average alignment of the optical anisotropy axes of the nanoparticle set, which increases with the average occupation of the nanoparticles by target molecules.

2. Measurement Cell.

The measurement cell contains, in an appropriate vehicle, the optically anisotropic nanoparticles and the substance to be analyzed, which may also contain nonspecific additive substances, besides the target molecules. Possible target molecules include biological substances, such as, for example, viruses, bacteria, nucleic acid sequences, antibodies, antigens or any other proteins, as well as dissolved inorganic or organic chemical substances, such as, for example, polymers.

The vehicle here is optically transparent at least in the wavelength range used for measuring the optical anisotropy of the nanoparticles. The measurement cell as well is optically transparent in this wavelength range, or it has windows through which light can be irradiated into the solution and coupled out.

3. Optically Anisotropic Nanoparticles.

The nanoparticles are as monodisperse as possible with regard to all their properties, and they possess at least one optical anisotropy property that allows the optical determination of the spatial alignment of the particle in the solution. In addition, by use of an external stimulus, i.e., particularly an electrically or magnetic field, a torque can be applied to the particles, to align them in a certain spatial direction.

The particles are in a stable suspension in an appropriate vehicle which contains the target molecules to be detected. Moreover, in at least one place, the surface of the particles is such that the target molecules can bind specifically to it or there.

The shape of the particles is preferably oblong, to satisfy the requirements with regard to optical anisotropy and alignability. However, deviating particle shapes are not excluded, such as, for example, spherical shapes, where, in this case, the required optical anisotropy and the alignability are the result of the internal structure of the particles, for example, of the crystalline anisotropy of the material and/or of an appropriate composite structure of several materials. A template that is well suited for oblong composite nanoparticles consists of carbon monotubes, for example, which can be filled and/or sheathed with appropriate materials, see Monthioux et al., Journal of Materials Research 21 (2006) 2774. Moreover, certain materials can also be added specifically to the nanotube ends, see Jiang et al., Journal of Electroceramics 17 (2006) 87.

The size of the particles is limited, on the one hand, by the requirement that the particles must remain stable in the vehicle used, i.e., they must not agglomerate or precipitate. On the other hand, the binding of the target molecules must lead to a measurable increase in the Brownian relaxation time, i.e., the maximum particle size is a function of the size of the target molecules to be detected. For both reasons only particles whose size in each dimension falls in the 1-1000 nanometer range can be used advantageously in practice.

Below, without limiting the general nature of the claim, several examples of optically anisotropic nanoparticles that can be used according to the invention are listed.

i) Metal Nanoparticles with Spectral Anisotropy

This class of particles contains all types of nanoparticles, in which the spectral distribution of the light that is scattered, emitted or quenched by the particles is a function of the spatial alignment of the optical anisotropy axes of the particles relative to a preferred direction. This preferred direction can be generated here by polarizers that polarize the incident light and/or the light to be analyzed.

A possible implementation of such particles consists, for example, of semiconducting quantum dots, rods or wires that present a spectrally anisotropic luminescence. Shan et al., for example, described CdSe nanowires whose emission spectrum consists of two bands whose relative intensity proportions are a function of whether the emitted light is viewed parallel or perpendicularly to the long axes of the nanowire, see Shan et al., Physical Review B 74 (2006) 153402.

A similar method can also be achieved with other substances, such as, organic fluorescent dyes, provided their spectrum has anisotropic properties.

Oblong metal nanoparticles are another example of nanoparticles with anisotropic spectral properties, where two mutually separate resonance frequencies occur for plasmon oscillations that are parallel or perpendicular to the light axis. As a function of the alignment of the long axis of the particles with respect to the polarization of the incident light, these two resonance frequencies are excited proportionally. By measuring the relative proportions of these two resonance frequencies in the extinction or scattering spectrum of the particle it is thus possible to determine the spatial alignment of the long particle axis relative to the polarization axis of the light that is incident on the particle and directed toward it, see, for example, Pérez-Juste et al., Adv. Funct. Mater. 15 (2005) 1065.

ii) Anisotropically Polarizing Nanoparticles.

Particles that have a polarization effect on scattered, emitted or quenched light represent an additional variant for optically anisotropic nanoparticles. Possible examples are, polarized luminescent particles, such as, semiconducting quantum dots, rods or wires. Elongated particles of this type present particularly a high polarization degree of the emitted light, starting at an aspect ratio of 2:1, see Hu et al., Science 292 (2001) 2060. Oblong metal nanoparticles, see Pérez-Juste et al., Coordination Chemistry Review 249 (2005) 1870, or mesomers of liquid crystals diluted in the solution can also polarize the incident light.

Now, if a preferred direction is induced by a polarizer or analyzer in the light path, then one can derive the spatial alignment of the particle from the polarization effect of the particle.

4. Optical Structure.

The optical structure is suitable for measuring the degree to which optical anisotropy has been induced by the nanoparticles, thus making it possible to derive the relaxation behavior of the particles. The precise structure is a function of the type of optical anisotropy that can be used for the measurement. A non-limiting example is given below, showing a possible optical structure for each one of the parameter values of spectrum and polarization.

i) Parameter Value Spectrum.

In this variant of the invention, the spatial alignment of the particles in the solution is determined from changes in their spectrum. The particles used here present an anisotropic extinction, emission or scattering spectrum, from which one can derive the alignment of the anisotropy axis relative to a preferred direction that is established by at least one polarizer.

As an example, a possible structure is described for measuring the relaxation behavior of elongated metal nanoparticles. The constitution of the particles here is such that plasmon resonances occur in them, where the resonance frequency $f_{par}$ for plasmon oscillations that are parallel to the long axis is spectrally separate from the resonance frequency $f_{senk}$ for plasmon oscillations that are perpendicular to the long axis of the particles. In addition, the constitution of the particles must be such that their long axis can be aligned along an external field.

The nanoparticles that are dispersed in the solution in the measurement cell are irradiated with linearly polarized light from a white light source. An external stimulus ensures a spatial alignment of the particles. During a temporal change in the amplitude and/or the direction of the external stimulus or field, the scattered or quenched light of the particle set is viewed through an appropriate filter in two separate detectors at the two characteristic plasmon resonance frequencies of the nanoparticles. From the recorded temporal course of the intensity ratio from the two detectors with a certain program for changing the external stimulus, it is then possible to determine the relaxation behavior of the nanoparticles, from which one can derive the average occupation of the particles by target molecules specifically bound to them.

This measurement principle can also be varied to the effect that, for the illumination of the particles, unpolarized light is used, and the preferred direction is generated later by an analyzer in the light path of the scattered or quenched light. An appropriate combination of several polarizers and analyzers is also conceivable within the context of the present invention. Moreover, other types of nanoparticles with spectral anisotropic extinction, emission or scattering can also be used.

ii) Parameter Value Polarization.

When using light polarizing nanoparticles, the polarization of the light that is scattered, emitted or quenched by the particles can be used for measuring the average spatial alignment of the particle set, to determine the relaxation of the particle following a change of the external stimulus.

In the context of a particularly simple measurement setup, the measurement cell is irradiated with unpolarized light from a white light source. As a function of the degree of the average spatial alignment of the particle set, one then gets a linear polarization portion, in the scattered or quenched light. The light exiting from the sample is now led through an analyzer on a detector, and the temporal change of the intensity signal under a change of the amplitude and/or direction of the external stimulus is recorded. From this, it is possible to determine in turn the relaxation behavior of the nanoparticles, and thus the average occupation of the particles by specifically bound target molecules.

Alternatively, instead of using an analyzer for the light exiting from the sample, the incident light can also be polarized by a polarizer, or an appropriate combination of several polarizers and analyzers can be used.

Other features which are considered as characteristic for the invention are set forth in the appended claims.

Although the invention is illustrated and described herein as embodied in an optical measurement method for molecular detection using relaxation measurement in optically anisotropic nanoparticles and device for performing the method, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
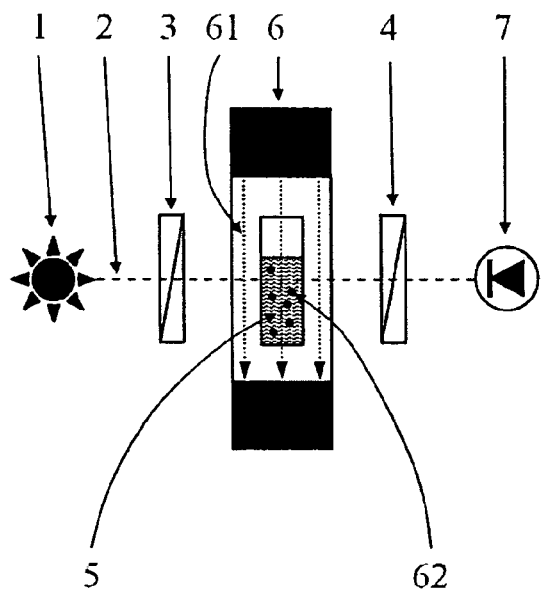
FIGS. 1 and 2 are illustrations showing possible embodiments of a measurement setup for a parameter value polarization according to the invention.
Figure 2:
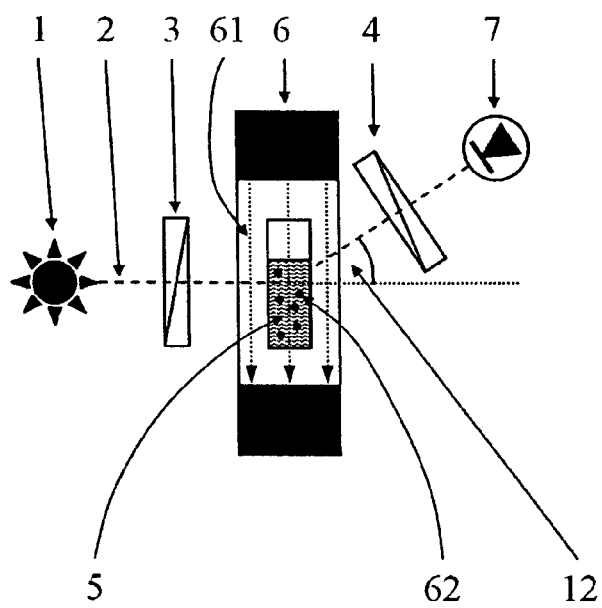
Figure 3:
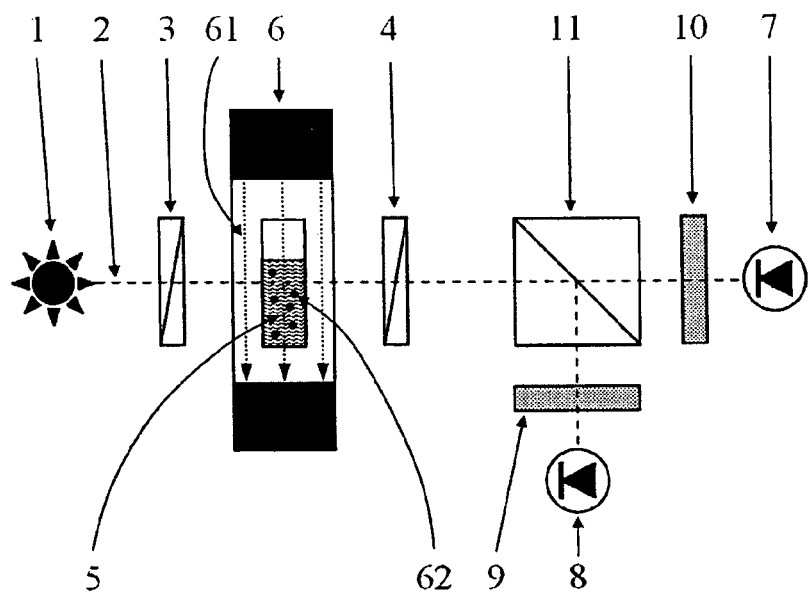
FIGS. 3 and 4 are illustration showing embodiments of the measurement setup for the parameter value spectrum.
Figure 4:
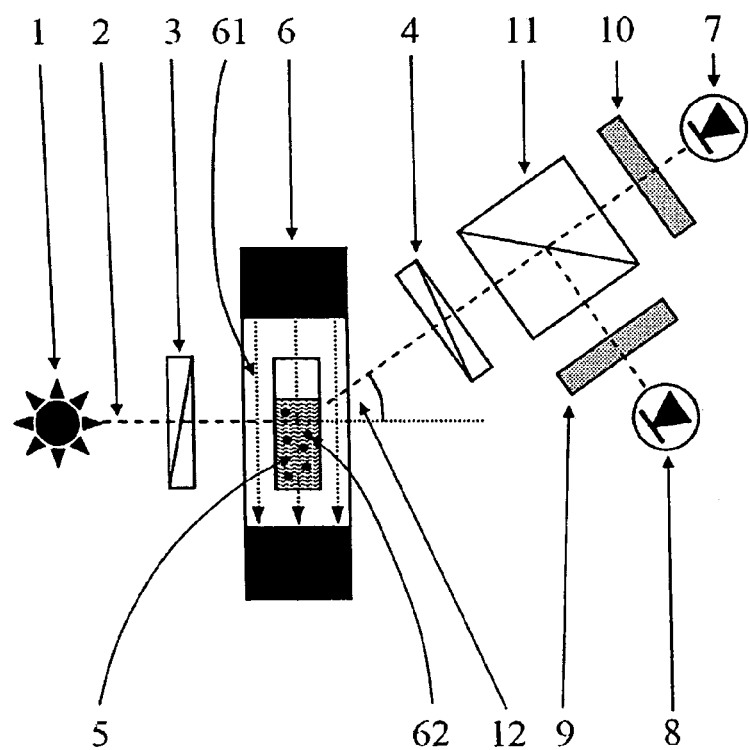

Here, FIG. 1 and FIG. 3 relate to measurements of an extinction, and FIG. 2 and FIG. 4 relate to measurements of the scattering or emission.

All the possible measurement setups share the feature that, using any light source 1, a parallel light beam 2 can be generated, which is directed on a measurement cell 5. The light source 1 can be monochromatic, i.e., a laser, for example, or polychromatic, i.e., a spiral-bound filament, for example, which emits polarized or unpolarized light.

The measurement cell 5 contains a solution containing, besides additive substances, the target molecules to be analyzed and optically anisotropic nanoparticles 62. The optical anisotropy axes of the nanoparticles can be aligned by an external stimulus, i.e., particularly by a field, which is generated by an appropriate electromagnetic field-generating apparatus 6, and whose field 61 can be changed with regard to its amplitude and/or direction.

Using at least one polarizer 3 and/or analyzer 4, at least one preferred direction is defined, relative to which the optical anisotropy induced by the nanoparticles is measured in a detector 7 as a function of the temporal change of the stimulus or field.

If the type of optical anisotropy induced by the nanoparticles is a polarization effect, then the above-described components are sufficient for the optical setup.

Appropriate examples are represented in FIG. 1 and FIG. 2, where FIG. 1 relates to the measurement of light that has been quenched by the nanoparticles. FIG. 2, on the other hand, shows a possible setup for measurements of scattering or emission, in which the analyzer light path is rotated through a spatial angle 12 with respect to the incident light beam 2.

FIG. 3 and FIG. 4, on the other hand, show examples of possible measurement setups for the case where the nanoparticles extinguish, scatter or emit spectrally anisotropic light. In this case, at least two wavelengths are chosen whose spectral intensity is characteristic for the spatial alignment of the nanoparticles. In the simplest case, the analysis is carried out here by use of a beam splitter 11, which splits the light that has been quenched, scattered or emitted by the nanoparticles into at least two separate light paths.

Subsequently, using color filters 9, 10, at least two characteristic spectral ranges are selected, and measured in the detectors 7, 8. The ratio of the light intensity measured by the at least two separate detectors 7, 8 allows the determination of the alignment of the nanoparticles, which is recorded as a function of the temporal change of the stimulus or field acting on them.

FIG. 3 relates to the measurement of light that has been quenched by the nanoparticles. FIG. 4, on the other hand, shows a possible setup for measurements of scattering or emission, in which the analyzer light path is rotated through a spatial angle 12 with respect to the incident light beam 2.

The invention claimed is:

1. A method for molecular detection via one of determination or a measurement of a relaxation behavior of particles selected from the group consisting of microparticles and nanoparticles, that are one of dispersed or suspended in a fluid medium, on a surface of the particles one of target molecules, molecule sequences, molecule parts or organisms are one of bound specifically or nonspecifically, which comprises the steps of:

provlding the particles that have been occupied to be alignable, at least predominantly, in a spatial direction, in the dispersion or the suspension, as a result of an influence of an external stimulus, for the determination of the relaxation behavior, in the suspension or the dispersion being used the particles have optical anisotropy, besides their geometric positional alignability, where the optical anisotropy of the particles originates from an anisotropic plasmon excitation in the particles;

converting the particles, in the dispersion or the suspension, either from an at first stochastic, statistically disordered, unaligned state, into a finally at least predominantly uniformly aligned state, or vice versa;

irradiating in light selected from the group consisting of linear light, polarized light and nonpolarized light into the suspension or the dispersion;

determining one of a behavior or properties of the dispersion or the suspension in each of the two states and/or between the two states resulting in a determined relaxation behavior by subjecting the light to an optometric analysis where the light is one of:
  taken up directly from the suspension or the dispersion in an irradiation direction in or by absorption;
  the light exiting as scattered light at an angle with respect to the irradiation direction; or
  the light that is emitted by excitation;

performing the optometric analysis at least one of immediately, after the light passes through a polarization filter connected after the dispersion or the suspension, or only after a forced passage through a polarization filter which is connected after the dispersion or the suspension through which the light passes; and deriving from the determined relaxation behavior at least one of a concentration, a size and a property of one of the target molecules, the molecule sequences, the molecule parts and the organisms bonded to the particles.

2. The method according to claim 1, which further comprises during the optometric analysis, at least one of optical polarization or an optical spectrum of the light that has been one of scattered, emitted or quenched by the particles in the dispersion, and particularly an intensity or change in intensity of the light, is used as a parameter value.

3. The method according to claim 1, which further comprises changing at least one of an amplitude or a direction of the external stimulus acting on the particles that have been occupied by one of the target molecules, the molecule sequence, the molecule part or the organism binding to the particles during a course of the measurement, and the relaxation of the particle toward or through a new equilibrium position given by a new changed stimulus is determined and recorded as a function of one of time, frequency or phase.

4. The method according to claim 3, wherein the external stimulus that acts on the particles that have been occupied by the target molecules in the dispersion or the suspension is one of kept discretely at a certain value and changed periodically.

5. The method according to claim 1, wherein in the dispersion or the suspension, one uses, as the nanoparticles that can be aligned by the external stimulus, one of semiconducting nanocrystals, quantum dots, nanoparticles with at least one of characteristic emission and absorption spectra, and nanoparticles made of noble metals in which plasmon resonances with characteristic scattering and/or extinction spectra, or changes in the latter, are excited by incident light.

6. The method according to claim 5, which further comprises selecting the quantum dots from the group consisting of CdSe nanocrystals and ZnS nanocrystals.

7. The method according to claim 5, which further comprises selecting the noble metals from the group consisting of Au and Ag.

8. The method according to claim 1, wherein in the dispersion or the suspension, one uses as the nanoparticles that are optically anisotropically magnetizable and alignable by an external magnetic field one of, particles that present intrinsically a magnetic moment, carbon nanotubes having magnetic components and represent magnet-composite nanoparticles with a core-sheath structure, carbon nanotubes that are filled completely or partially with magnetic material, oblong particles, elongated particles, or nanotubes with magnetic materials on at least one of their poles or ends.

9. The method according to claim 1, wherein in the dispersion or the suspension, one uses optically anisotropic nanoparticles that are alignable by the external stimulus, including by an external field, and have one of a crystalline shape, an amorphous/spherical shape or elongated shape, and further have in at least one of three dimensions in each case a size of 1-1000 nm.

10. The method according to claim 9, which further comprises setting the size to be 2-100 nm.

11. The method according to claim 1, wherein the target molecules, the molecule sequences, the molecule parts or the organisms that are bound to the optically anisotropic nanoparticles or on the surface in the dispersion or the suspension are selected from the group consisting of viruses, bacteria, nucleic acid sequences, antibodies, antigens, proteins, molecules, chemical compounds, oligomer molecules and polymer molecules.

12. The method according to claim 1, wherein for the dispersion or the suspension for the anisotropic or anisotropized nanoparticles, one uses, as the fluid medium, a fluid which is at least partially optically transparent at least in a wavelength range that is used for a determination of an optical anisotropy of the particles distributed in the fluid.

13. The method according to claim 1, which further comprises ascertaining a relaxation time as the relaxation behavior.

14. The method according to claim 1, which further comprises providing an aligned field as the external stimulus.

15. The method according to claim 1, which further comprises providing at least one of an electrical field or a magnetic field as the external stimulus.

16. The method according to claim 1, which further comprises determining one of the behavior or the properties of the dispersion or the suspension in a time between the two states.

* * * * *